(12) United States Patent
Kessinger et al.

(10) Patent No.: US 7,399,876 B2
(45) Date of Patent: Jul. 15, 2008

(54) PREPARATION OF AN ALKENYLPHOSPHONIC ACID DERIVATIVE

(75) Inventors: Roland Kessinger, Weinheim (DE); Jan-Dirk Arndt, Mannheim (DE); Jochem Henkelmann, Mannheim (DE); Florian Thomas, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 396 days.

(21) Appl. No.: 10/977,436

(22) Filed: Nov. 1, 2004

(65) Prior Publication Data

US 2005/0113593 A1 May 26, 2005

(30) Foreign Application Priority Data

Oct. 30, 2003 (DE) .................... 103 50 674

(51) Int. Cl.
*C07F 9/02* (2006.01)
(52) U.S. Cl. ............... 558/137; 558/134; 502/162
(58) Field of Classification Search .......... 558/137, 558/134; 502/162
See application file for complete search history.

(56) References Cited

U.S. PATENT DOCUMENTS

| 3,673,285 A | 6/1972 | Lin |
| 3,972,923 A | 8/1976 | Finke et al. |
| 4,388,252 A | 6/1983 | Duersch et al. |
| 4,493,803 A | 1/1985 | Kleiner et al. |
| 5,693,826 A | 12/1997 | Tanaka et al. |
| 6,111,127 A | 8/2000 | Tanaka et al. |
| 7,479,798 | 12/2002 | Henkehmann et al. |
| 6,534,669 B2 * | 3/2003 | Henkelmann et al. ....... 558/137 |

FOREIGN PATENT DOCUMENTS

| DE | 2132 962 | 7/1973 |
| DE | 31 20 437 | 12/1982 |
| EP | 032 663 | 7/1981 |
| EP | 1 203 773 | 5/2002 |
| WO | 98/46613 | 10/1998 |
| WO | 99/67259 | 12/1999 |
| WO | 03/097654 | 11/2003 |
| WO | WO03/097654 | * 11/2003 |

OTHER PUBLICATIONS

Han et al., 2003, CAS: 139:396059.*
JACS Communications, Han et al., 2004, 126,5080-5081.

* cited by examiner

*Primary Examiner*—Rei-tsang Shiao
(74) *Attorney, Agent, or Firm*—Novak Druce + Quigg LLP

(57) ABSTRACT

Process for preparing an alkenylphosphonic acid derivative by reacting a phosphonic acid derivative with an alkyne in the presence of a catalyst complex system, wherein the catalyst complex system comprises
 (a) nickel,
 (b) a phosphine having at least two trivalent phosphorus atoms and in addition
 (c) a phosphine having one trivalent phosphorus atom.

12 Claims, No Drawings

PREPARATION OF AN ALKENYLPHOSPHONIC ACID DERIVATIVE

The present invention relates to a process for preparing an alkenylphosphonic acid derivative by reacting a phosphonic acid derivative with an alkyne in the presence of a catalyst complex system.

Vinylphosphonic acid derivatives, in particular dialkyl vinylphosphonates, are important as precursors for the preparation of vinylphosphonic acids and as monomers for copolymerization for the preparation of adhesives and flame-resistant plastics.

Various methods of preparing them are known.

The process described in DE-A 21 32 962 starts out from ethylene oxide and phosphorus trichloride. The tris(2-chloroethyl) phosphite obtained initially as reaction product is rearranged at 140-200° C. to form bis(2-chloroethyl) 2-chloroethanephosphonate and is then reacted with phosgene in the presence of a catalyst to give 2-chloroethanephosphonyl dichloride and vinylphosphonyl dichloride. Catalysts which can be used are amines, heterocyclic nitrogen compounds and phosphines and also phosphine oxides.

EP 32 663 A2 describes a process for preparing vinylphosphonic acid derivatives in which dialkyl 2-acetoxyethanephosphonates are dissociated in the presence of acidic or basic catalysts. Basic catalysts proposed are tertiary amines and phosphines, ammonium salts or phosphonium salts, heterocyclic compounds and acid amides. A disadvantage of the process is the formation of a mixture of vinylphosphonic acid derivatives. The proportion of dialkyl vinylphosphonates is not more than 23%.

An improved variant of this process which is described in DE 31 20 437 A1 comprises reacting the product mixture obtained with ortho esters of carboxylic acids to form dialkyl vinylphosphonates.

Disadvantages of the above processes are the formation of product mixtures, complicated, multistage syntheses, the necessity of using high reaction temperatures and the use of chlorinated starting compounds. The large proportion of by-products in particular has a serious adverse effect on the process economics.

A further synthetic route for preparing diesters of alkenylphosphonic acids is the addition of alkynes onto phosphonic diesters in the presence of a palladium complex as catalyst. An advantage of this synthetic route is a pure addition reaction without formation of stoichiometric amounts of by-products or coproducts.

U.S. Pat. No. 5,693,826 and WO 98/46613 disclose the addition reaction in the presence of a palladium complex having phosphines and phosphites as ligands at less than or equal to 100° C.

WO 99/67259 and U.S. Pat. No. 6,111,127 disclose bidentate phosphines as ligands.

A disadvantage of these processes is the use of expensive noble metal catalysts.

U.S. Pat. No. 3,673,285 describes the addition of alkynes onto phosphonic diesters to form alkenylphosphonic diesters at from 130 to 200° C. in the presence of nickel complexes selected from the group consisting of dicarbonylbis(triphenylphosphine)nickel(0), bis(tris(hydroxymethyl)phosphine)nickel(II) chloride, bis(tri-n-butylphosphine)nickel(II) bromide and tetracarbonylnickel(0). In the addition of ethyne onto diethyl phosphite in the presence of bis(tri-n-butylphosphine)nickel(II) bromide, a yield of diethyl vinylphosphonate of 40% was achieved (example 15). Disadvantages of this process are a low yield of significantly below 50% and the high reaction temperature of up to 200° C., which leads to exothermic decomposition of the ethyl phosphonate.

EP-A1-1 203 773 (BASF Aktiengesellschaft) describes a process for preparing alkenylphosphonic acid derivatives by reacting phosphonic acid derivatives with alkynes in the presence of a catalyst complex system, in which a catalyst complex system comprising (a) nickel and (b) a phosphine having at least two trivalent phosphorus atoms is used.

A disadvantage of this process is the amount of phosphines having at least two trivalent phosphorus atoms required (2:1 molar based on Ni), since these phosphines firstly have to be prepared from the corresponding phosphines having one trivalent phosphorus atom, which costs money.

A parallel BASF patent application having the same filing date relates to a process for preparing an alkenylphosphonic acid derivative by reacting a phosphonic acid derivative with an alkyne in the presence of a catalyst complex system comprising (a) nickel and (b) a phosphine having at least two trivalent phosphorus atoms and for (c) a phosphine having one trivalent phosphorus atom and the alkyne is added only after the phosphonic acid derivative has been brought into contact with the catalyst complex system for at least one minute.

It is an object of the present invention to find a process for preparing alkenylphosphonic acid derivatives which overcomes the disadvantages of the prior art, forms no coproducts, allows a reaction temperature of significantly below 200° C., makes a high yield of significantly above 50%, in particular above 75%, possible, does without the use of an expensive noble metal catalyst and gives catalyst costs which are lower than those in EP-A1-1 203 773.

We have found that this object is achieved by a process for preparing an alkenylphosphonic acid derivative by reacting a phosphonic acid derivative with an alkyne in the presence of a catalyst complex system, wherein the catalyst complex system comprises (a) nickel, (b) a phosphine having at least two trivalent phosphorus atoms and in addition (c) a phosphine having one trivalent phosphorus atom.

Thus, important aspects of the process of the present invention are the presence of a catalyst complex system comprising (a) nickel and (b) a phosphine having at least two trivalent phosphorus atoms and in addition (c) a phosphine having one trivalent phosphorus atom.

In particular, the nickel (a) is present in the catalyst complex system in the oxidation state zero [=Ni(O)].

In customary terminology, phosphines having one trivalent phosphorus atom are referred to as monophosphines, phosphines having two trivalent phosphorus atoms are referred to as diphosphines, phosphines having three trivalent phosphorus atoms are referred to as triphosphines, etc.

In general, the phosphines having at least two trivalent phosphorus atoms which are used in the process of the present invention have the formula (I)

where $R^1$, $R^2$, $R^3$ and $R^4$ are each, independently of one another, a carbon-containing organic radical and X is a carbon-containing organic bridging group.

For the purposes of the present invention, a carbon-containing organic radical is an unsubstituted or substituted, aliphatic, aromatic or araliphatic radical having from 1 to 30 carbon atoms. This radical can contain one or more heteroatoms such as oxygen, nitrogen, sulfur or phosphorus, for example —O—, —S—, —NR—, —CO—, —N═, —PR— and/or —PR$_2$ and/or be substituted by one or more functional groups containing, for example, oxygen, nitrogen, sulfur and/or halogen, for example by fluorine, chlorine, bromine, iodine and/or a cyano group (the radical R here is likewise a carbon-containing organic radical). If the carbon-containing organic radical contains one or more heteroatoms, it can also be bound via a heteroatom. Thus, for example, ether, thioether and tertiary amino groups are also included. The carbon-containing organic radical can be a monovalent or polyvalent, for example divalent, radical.

For the purposes of the present invention, a carbon-containing organic bridging group is an unsubstituted or substituted, aliphatic, aromatic or araliphatic divalent group having from 1 to 20 carbon atoms and from 1 to 10 atoms in the chain. The organic bridging group can contain one or more heteroatoms such as oxygen, nitrogen, sulfur or phosphorus, for example —O—, —S—, —NR—, —CO—, —N═, —PR— and/or —PR$_2$ and/or be substituted by one or more functional groups containing, for example, oxygen, nitrogen, sulfur and/or halogen, for example by fluorine, chlorine, bromine, iodine and/or a cyano group (the radical R here is likewise a carbon-containing organic radical). If the organic bridging group contains one or more heteroatoms, it can also be bound via a heteroatom. Thus, for example, ether, thioether and tertiary amino groups are also included.

In the process of the present invention, preference is given to using a phosphine (I) in which the radicals R$^1$, R$^2$, R$^3$ and R$^4$ are each, independently of one another, an unbranched or branched, acyclic or cyclic, unsubstituted or substituted alkyl radical which has from 1 to 20 aliphatic carbon atoms and in which one or more of the CH$_2$ groups may also be replaced by heteroatoms such as —O— or by heteroatom-containing groups such as —CO—or —NR— and one or more of the hydrogen atoms may be replaced by substituents such as aryl groups;

an unsubstituted or substituted aromatic radical which has one ring or two or three fused rings and in which one or more ring atoms may be replaced by heteroatoms such as nitrogen and one or more of the hydrogen atoms may be replaced by substituents such as alkyl or aryl groups;

or in which the radicals R$^1$ together with R$^2$ and/or R$^3$ together with R$^4$ form an unsubstituted or substituted, aliphatic, aromatic or araliphatic group having from 3 to 10 atoms in the chain.

Examples of preferred monovalent radicals R$^1$, R$^2$, R$^3$ and R$^4$ are methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl, 2-methoxy-2-propyl, methoxy, ethoxy, 1-propoxy, 2-propoxy (sec-propoxy), 1-butoxy, 2-butoxy (sec-butoxy), 2-methyl-1-propoxy (isobutoxy), 2-methyl-2-propoxy (tert-butoxy), 1-pentoxy, 2-pentoxy, 3-pentoxy, 2-methyl-2-butoxy (tert-amoxy), 1-hexoxy, 2-hexoxy, 3-hexoxy, 2-methyl-2-pentoxy, 3-methyl-3-pentoxy, phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl and 8-isoquinolyl.

Examples of preferred divalent radicals R$^1$ together with R$^2$ and/or R$^3$ together with R$^4$ are 1,4-butylene, 1,4-dimethyl-1,4-butylene, 1,1,4,4-tetramethyl-1,4-butylene, 1,4-dimethoxy-1,4-butylene, 1,4-dimethyl-1,4-dimethoxy-1,4-butylene, 1,5-pentylene, 1,5-dimethyl-1,5-pentylene, 1,5-dimethoxy-1,5-pentylene, 1,1,5,5-tetramethyl-1,5-pentylene, 1,5-dimethyl-1,5-dimethoxy-1,5-pentylene, 3-oxa-1,5-pentylene, 3-oxa-1,5-dimethyl-1,5-pentylene, 3-oxa-1,5-dimethoxy-1,5-pentylene, 3-oxa-1,1,5,5-tetramethyl-1,5-pentylene, 3-oxa-1,5-dimethyl-1,5-dimethoxy-1,5-pentylene,

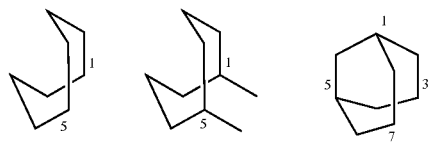

1,5-cyclooctylene, 1,5-dimethyl-1,5-cyclooctylene, 3,7-bicyclo[3.3.1]nonylene,

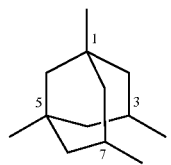

1,3,5,7-tetramethyl-3,7-bicyclo[3.3.1]nonylene,

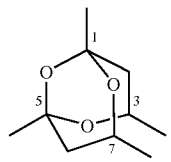

4,8,9-trioxa-1,3,5,7-tetramethyl-3,7-bicyclo[3.3.1]nonylene.

The process of the present invention is particularly preferably carried out using a phosphine (I) in which R$^1$, R$^2$, R$^3$ and/or R$^4$ are each, independently of one another, an unsubstituted or substituted C$_3$-C$_{12}$-alkyl radical in which not more than one atom from the group consisting of hydrogen, fluorine, chlorine, bromine and iodine is bound to the a carbon atom; and/or R$^1$, R$^2$, R$^3$ and/or R$^4$ are each, independently of one another, an unsubstituted or substituted aromatic radical which has six ring atoms and in which one, two or three ring atoms may be replaced by nitrogen; and/or in which R$^1$ together with R$^2$ and/or R$^3$ together with R$^4$ form an unsubstituted or substituted, aliphatic, aromatic or araliphatic group which has from 4 to 7 atoms in the chain and a total of not more than 30 carbon atoms.

The unsubstituted or substituted C$_3$- to C$_{12}$-alkyl radical in which not more than one atom from the group consisting of hydrogen, fluorine, chlorine, bromine and iodine is bound to the α carbon atom is an alkyl radical which is branched at the α carbon atom. Preference is given to at least two further carbon atoms being bound to the α carbon atom. The third atom bound to the α carbon atom is preferably hydrogen, carbon or a heteroatom such as oxygen, nitrogen or sulfur. Preferred examples are 2-propyl (sec-propyl), 2-butyl (sec-butyl), 2-methyl-2-propyl (tert-butyl), 2-methyl-2-butyl (tert-amyl) and 2-methoxy-2-propyl.

Preferred examples of unsubstituted or substituted aromatic radicals which have six ring atoms and in which one, two or three ring atoms may be replaced by nitrogen are phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl and 2-pyridyl.

Preferred examples of divalent radicals $R^1$ together with $R^2$ and/or $R^3$ together with $R^4$ are 1,1,4,4-tetramethyl-1,4-butylene, 1,4-dimethyl-1,4-dimethoxy-1,4-butylene, 1,1,5,5-tetramethyl-1,5-pentylene, 1,5-dimethyl-1,5-dimethoxy-1,5-pentylene, 1,5-dimethyl-1,5-cyclooctylene, 1,3,5,7-tetramethyl-3,7-bicyclo[3.3.1]nonylene and 4,8,9-trioxa-1,3,5,7-tetramethyl-3,7-bicyclo[3.3.1]nonylene.

Very particular preference is given to using a phosphine (I) in which the radicals $R^1$, $R^2$, $R^3$ and $R^4$ are each a 2-methyl-2-propyl (tert-butyl) or phenyl group in the process of the present invention.

In the process of the present invention, preference is given to using a phosphine (I) in which X is an unsubstituted or substituted, aliphatic, aromatic or araliphatic group which has from 1 to 8 atoms, preferably from 2 to 4 atoms, in the chain and a total of not more than 20 carbon atoms. In this group, one or more of the $CH_2$ groups may be replaced by heteroatoms such as —O— or heteroatom-containing groups such as —CO— or —NR— and/or one or more of the aromatic ring atoms may be replaced by heteroatoms such as nitrogen.

Examples of preferred bridging groups X are 1,2-ethylene, 1,3-propylene, 1,2-propylene, 1,4-butylene, 2-methyl-1,3-propylene, 1,5-pentylene, 2,2-dimethyl-1,3-propylene, 1,6-hexylene, —O—$CH_2$$CH_2$—O—, —O—$CH_2$$CH_2$$CH_2$—O—, o-phenylene, o-xylylene (=ortho —$CH_2$—$C_6H_4$—$CH_2$—) and 2,2'-biphenylene.

The process of the present invention is particularly preferably carried out using a phosphine (I) in which the bridging group X is a 1,2-ethylene, 1,3-propylene, 1,4-butylene or o-xylylene group.

Very particular preference is given to using a phosphine (I) in which the radicals $R^1$ to $R^4$ are each a 2-methyl-2-propyl (tert-butyl) or phenyl group and X is a 1,2-ethylene, 1,3-propylene, 1,4-butylene or o-xylylene group in the process of the present invention.

Very particularly preferred examples are 1,2-bis(di-tert-butylphosphino)ethane, 1,2-bis(diphenylphosphino)ethane, 1,3-bis(di-tert-butylphosphino)propane, 1,3-bis(diphenylphosphino)propane, 1,4-bis(di-tert-butylphosphino)butane, 1,4-bis(diphenylphosphino)butane, bis(di-tert-butylphosphino)o-xylene and bis(diphenylphosphino)-o-xylene, in particular 1,3-bis(di-tert-butylphosphino)propane and 1,3-bis(diphenylphosphino)propane.

The synthesis of diphosphines is generally known and is described, for example, in L. Brandsma et al., "Application of Transition Metal Catalysts in Organic Synthesis", Springer-Verlag, Berlin 1997, pages 6 to 9.

The additional phosphine having one trivalent phosphorus atom (c) in the Ni catalyst system is generally a phosphine of the formula (IV)

where $R^9$, $R^{10}$, $R^{11}$ are each, independently of one another, a carbon-containing organic radical.

For the purposes of the present invention, a carbon-containing organic radical is an unsubstituted or substituted, aliphatic, aromatic or araliphatic radical having from 1 to 30 carbon atoms. This radical may contain one or more heteroatoms such as oxygen, nitrogen, sulfur or phosphorus, for example —O—, —S—, —NR—, —CO—, —N=, —PR— and/or —$PR_2$ and/or be substituted by one or more functional groups containing, for example, oxygen, nitrogen, sulfur and/or halogen, for example by fluorine, chlorine, bromine, iodine and/or a cyano group (the radical R here is likewise a carbon-containing organic radical). If the carbon-containing organic radical contains one or more heteroatoms, it can also be bound via a heteroatom. Thus, for example, ether, thioether and tertiary amino groups are also included. The carbon-containing organic radical can be a monovalent or polyvalent, for example divalent, radical.

$R^9$, $R^{10}$, $R^{11}$ are preferably (independently of $R^{1-4}$) radicals and groups as defined above for $R^{1-4}$.

Very particular preference is given to $R^9$, $R^{10}$, $R^{11}$ each being a $C_{3-6}$-cycloaliphatic and/or aromatic radical such as cyclohexyl or phenyl.

The phosphine having a trivalent phosphorus atom (c) and the formula (IV) in the Ni catalyst system is, in a preferred embodiment, triphenylphosphine and/or tricyclohexylphosphine.

In the process of the present invention, the catalyst complex system is generally prepared by combining an Ni(O) complex and the two phosphines (b, c), in particular the two phosphines of the formulae I and IV, or by combining an Ni(II) compound, a reducing agent and the two phosphines (b, c), in particular the two phosphines of the formulae I and IV.

Since the respective phosphonic acid derivative can also act as reducing agent, the catalyst complex system can also be obtained by combining an Ni(II) compound and the two phosphines (b, c), in particular the two phosphines of the formulae I and IV, and a phosphonic acid derivative without a further reducing agent.

When carrying out the first-named variant, it is in principle possible to use all Ni(O) complexes which react with the phosphine under the reaction conditions to form a catalyst complex system. Examples of suitable Ni complexes are tetracarbonylnickel, bis(cycloocta-1,5-diene)nickel and (cyclododeca-1,5,9-triene)nickel.

The Ni(II) compounds required for the second variant can be of an inorganic, organic or mixed nature. Examples are nickel(II) halides (e.g. $NiCl_2$), nickel(II) sulfate, nickel(II) acetylacetonate, 1,3-bis(diphenylphosphino)propanenickel (II) chloride, hexamminenickel(II) chloride, nickel(II) bromide•diethylene glycol dimethyl ether complexes, dimethyinickel(II) complexes $(CH_3)_2NiL_2$ (L=for example, triphenylphosphine, triethylphosphine, tributylphosphine) and dimethylnickel(II) complexes $(CH_3)_2NiL$ (L=for example, tetramethylethylenediamine (TMEDA), bis(diphenylphosphino)propane, bis(diphenylphosphino)butane). Suitable reducing agents are, for example, elemental zinc, trialkylboron compounds, trialkylaluminum compounds, diisobutylaluminum hydride and phosphonic acid derivatives.

The catalyst complex system can be prepared in a separate step prior to the actual alkenylation of the phosphonic acid derivative or in situ by combining the abovementioned components.

The temperature in the preparation of the catalyst-complex system is generally from 30 to 120° C., preferably from 60 to 110° C.

As solvent, it is generally possible to use the phosphonic acid derivative as long as this is liquid under the reaction conditions. However, it is also possible and may be advantageous to prepare the catalyst complex system in the presence of a further, inert solvent. In this case, preference is given to using the same solvents which can also be used as solvents for the alkenylation reaction and are described in more detail below.

In the process of the present invention, it is usual to employ a molar ratio of the two phosphines (total number of moles) to the nickel of the catalyst complex system of from 0.5 to 6, preferably from 1 to 4 and particularly preferably from 2.5 to 3.5.

The molar ratio of the nickel of the catalyst complex system and the phosphorus of the phosphonic acid derivative and the products formed therefrom is generally from 0.01 to 10%, preferably from 0.05 to 5% and particularly preferably from 0.05 to 3%, in the process of the present invention.

The molar ratio of nickel:(phosphine having at least two trivalent phosphorus atoms):(phosphine having one trivalent phosphorus atom) is preferably 1:(0.5-2):(1-4), in particular 1: (1-1.3):(1.5-2).

The process of the present invention can be carried out at from 0 to 200° C., preferably from 20 to 150° C., particularly preferably from 50 to 120° C., in particular from 50 to 100° C.

It is generally carried out at a pressure of from 0.01 to 5 MPa abs., preferably from 0.05 to 2.5 MPa abs., particularly preferably from 0.05 to 0.14 MPa abs., in particular at atmospheric pressure.

The process of the present invention can be carried out in the absence of an additional solvent ("solvent-free") or in the presence of an inert solvent. For the purposes of the present invention, inert solvents are solvents which do not react chemically with the compounds used under the reaction conditions set. Suitable inert solvents are, for example, tetrahydrofuran, 1,4-dioxane, N-methylpyrrolidone, N-methylpiperidone, dimethyl sulfoxide, toluene, xylene, glycol ethers (e.g. 1,2-dimethoxyethane (ethylene glycol dimethyl ether), bis(2-methoxyethyl) ether (diethylene glycol dimethyl ether), triethylene glycol dimethyl ether or tetraethylene glycol dimethyl ether), dimethylformamide, dimethylformanilide, chlorobenzene and mixtures thereof. The addition of an inert solvent can, for example, be advantageous when using relatively high molecular weight phosphonic acid derivatives which are viscous or solid under the reaction conditions.

It may be advantageous to carry out the process of the present invention in the presence of a free-radical inhibitor as additive. In principle, suitable free-radical inhibitors are the inhibitors customary in industry, for example N,N'-bis(1-methylpropyl)-1,4-phenylenediamine, 2,6-di-tert-butyl-4-methylphenol or 1,2-dihydroxybenzene (catechol). If a free-radical inhibitor is used, the molar ratio of the free-radical inhibitor to the phosphorus of the phosphonic acid derivative and the products formed therefrom is generally from 0.01 to 10%, preferably from 0.05 to 5% and particularly preferably from 0.5 to 3%.

The phosphonic acid derivatives to be used in the process of the present invention are generally known and have, for example, the formula (II)

where $R^5$ and $R^6$ are each, independently of one another, a carbon-containing organic radical. For the definition of the term "carbon-containing organic radical", reference is made to what has been said above with regard to the definition of the radicals $R^1$ to $R^4$ in the formula (I).

$R^5$, $R^6$ are preferably (independently of $R^{1-4}$) radicals and groups as have been defined above for $R^{1-2}$.

Phosphonic acid derivatives of the formula (II) are generally prepared by reacting phosphorus trichloride with the corresponding alcohols and/or the corresponding phenols. Further details may be found, for example, in Ullmann's Encyclopedia of Industrial Chemistry, 6$^{th}$ edition, 1999 Electronic Release, Chapter "Phosphorus Compounds, Organic-Phosphites and Hydrogenphosphonates".

In the process of the present invention, preference is given to using a phosphonic acid derivative (II) in which the radicals $R^5$ and $R^6$ are each, independently of one another, an unbranched or branched, acyclic or cyclic, unsubstituted or substituted alkyl radical which has from 1 to 20 aliphatic carbon atoms and in which one or more of the $CH_2$ groups may also be replaced by heteroatoms such as —O— or by heteroatom-containing groups such as —CO— or —NR— and one or more of the hydrogen atoms may be replaced by substituents such as aryl (e.g. phenyl), alkyl (e.g. $C_{1-10}$-alkyl), hydroxyalkyl (e.g. $C_{1-10}$-hydroxyalkyl), haloalkyl (e.g. $C_{1-10}$haloalkyl), acetoxyalkyl (e.g. acetoxy-$C_{1-10}$-alkyl);

an unsubstituted or substituted aromatic radical which has one ring or two or three fused rings and in which one or more ring atoms may be replaced by heteroatoms such as nitrogen and one or more of the hydrogen atoms may be replaced by substituents such as alkyl or aryl groups;

or in which the radicals $R^5$ together with $R^6$ form an unbranched or branched, acyclic or cyclic, unsubstituted or substituted $C_4$-$C_{20}$-alkylene radical which has from 4 to 10 atoms in the alkylene chain and in which $CH_2$ groups may also be replaced by heterogroups such as —CO—, —O— or —NR— and one or more of the hydrogen atoms may be replaced by substituents such as aryl groups.

Examples of preferred radicals $R^5$ and $R^6$ are $C_1$-$C_{12}$-alkyl, particularly preferably methyl, ethyl, 1-propyl, 2-propyl, 1-butyl, 2-butyl, 2-methyl-1-propyl, 2-methyl-2-propyl, 1-pentyl, 1-hexyl, 1-octyl, 2-ethyl-1-hexyl, 1-decyl and 1-dodecyl;

$C_6$-$C_{10}$-aryl, particularly preferably phenyl;

$C_7$-$C_{10}$-aralkyl, particularly preferably phenylmethyl; and $C_7$-$C_{10}$-alkaryl, particularly preferably 2-methylphenyl, 3-methylphenyl and 4-methylphenyl.

Very particular preference is given to using the dimethyl ester, the diethyl ester, the dipropyl ester, the dibutyl ester, the di(2-ethylhexyl) ester or the diphenyl ester of phosphonic acid as phosphonic acid derivative in the process of the present invention.

The alkynes used in the process of the present invention have the formula (III)

where $R^7$ and $R^8$ are each, independently of one another, hydrogen or a carbon-containing organic radical. $R^7$ and $R^8$ may also, if desired, be joined to one another. For the definition of the term "carbon-containing organic radical", reference is made to what has been said above with regard to the definition of the radicals $R^1$ to $R^4$ in the formula (I).

$R^7$, $R^8$ are preferably (independently of $R^{1-4}$) radicals and groups as have been defined above for $R^{1-2}$.

The process of the invention is preferably carried out using an alkyne (III) in which the radicals $R^7$ and $R^8$ are each, independently of one another, hydrogen (H);

an unbranched or branched, acyclic or cyclic, unsubstituted or substituted alkyl radical which has from 1 to 20 aliphatic carbon atoms and in which one or more of the $CH_2$ groups may also be replaced by heteroatoms such as —O— or by heteroatom-containing groups such as —CO— or —NR— and in which one or more of the hydrogen atoms may be replaced by substituents such as aryl groups;

an unsubstituted or substituted aromatic radical which has one ring or two or three fused rings and in which one or more ring atoms may be replaced by heteroatoms such as nitrogen and one or more of the hydrogen atoms may be replaced by substituents such as alkyl or aryl groups.

Examples of preferred radicals $R^7$ and $R^8$ are hydrogen (H);

$C_1$-$C_{10}$-alkyl, particularly preferably methyl, ethyl, 1-propyl, 1-butyl, 1-pentyl and 1-hexyl;

$C_6$-$C_{10}$-aryl, particularly preferably phenyl;

$C_7$-$C_{10}$-aralkyl, particularly preferably phenylmethyl; and $C_7$-$C_{10}$-alkaryl, particularly preferably 2-methylphenyl, 3-methylphenyl and 4-methylphenyl.

Very particular preference is given to using ethyne or propyne as alkynes in the process of the present invention.

The process of the present invention is very particularly preferably used to prepare dimethyl ethenylphosphonate, diethyl ethenylphosphonate, di-n-propyl ethenylphosphonate and di-n-butyl ethenylphosphonate.

When, for example, phenylacetylene or, for example, 1-octyne and dimethyl phosphite are used, three isomeric alkenylphosphonic diesters can be formed as reaction products in accordance with the following reaction equation (R'=phenyl or R'=n-hexyl):

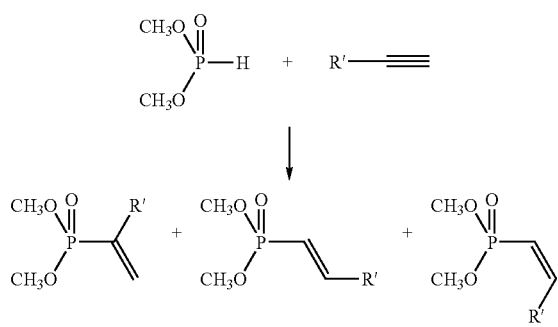

The process of the present invention can be carried out batchwise, semicontinuously or continuously.

In an example of a batch process, the two phosphines (b, c), in particular the two phosphines of the formulae I and IV, the Ni complex (or the Ni(II) compound and the reducing agent), the phosphonic acid derivative, if desired a solvent and if desired a free-radical inhibitor are combined, mixed and brought to the reaction conditions. After a short time, generally after from 1 to 60 minutes, preferably from 5 to 30 minutes, the alkyne is added to the reaction mixture which has been brought to the reaction conditions. After the reaction is complete, the reaction mixture is passed to the work-up, preferably by distillation, and the desired alkenylphosphonic acid derivative is isolated.

In an example of a semicontinuous process, the two phosphines (b, c), in particular the two phosphines of the formulae I and IV, the Ni complex (or the Ni(II) compound and the reducing agent), the phosphonic acid derivative, if desired a solvent and if desired a free-radical inhibitor are combined, mixed and brought to the reaction temperature. The alkyne is then, preferably after the reaction mixture has been maintained at the reaction temperature for a short time, generally from 1 to 60 minutes, preferably from 5 to 30 minutes, fed in continuously until the desired amount has been reached. It is advantageous to add the alkyne after the two phosphines (b, c), the Ni complex (or the Ni(II) compound and the reducing agent) and the phosphonic acid derivative have been combined, mixed and brought to the reaction conditions. The alkyne can be introduced in gaseous or liquid form. When it is added in liquid form, pure, liquid alkyne or a solution in a solvent can be used. After the addition of alkyne is complete, the reaction mixture can be left under the reaction conditions for a further time. After the reaction is complete, the reaction mixture is passed to the work-up, preferably by distillation, and the desired alkenylphosphonic acid derivative is isolated.

In an example of a continuous process, the two phosphines (b, c), in particular the two phosphines of the formulae I and IV, the Ni complex (or the Ni(II) compound and the reducing agent), if desired a solvent and if desired a free-radical inhibitor are combined, mixed and brought to the reaction temperature. The phosphonic acid derivative and the alkyne are then added continuously in the desired ratio. The phosphonic acid derivative is generally added in liquid form, if appropriate as a solution in a solvent. The alkyne can be introduced in gaseous or liquid form. When it is added in liquid form, it is possible to use pure, liquid alkyne or a solution in a solvent. Liquid reaction mixture is taken off continuously and the alkenylphosphonic acid derivative formed is isolated in a downstream stage, for example by distillation or extraction. If desired, relatively high boiling by-products are also separated off. The remaining mixture, which comprises mainly unreacted phosphonic acid derivative and any solvent used, can, if desired, be recirculated.

The process of the present invention makes it possible to prepare alkenylphosphonic acid derivatives from readily available starting compounds in only one synthesis step at a reaction temperature of preferably below 150° C. without use of an expensive noble metal catalyst. Since the reaction is a very selective addition reaction, no coproducts and only a small amount of by-products are formed. The process of the present invention allows a high yield of significantly above 50%, in particular above 75%, at catalyst costs which are reduced compared to EP-A1-1203 773 to be achieved with good process economics.

EXAMPLES

Example 1

27.50 g of dimethyl phosphite were admixed with 27 ml of tetraethylene glycol dimethyl ether in a three-necked flask provided with an internal thermometer, condenser and gas inlet tube and the mixture was degassed under argon. After addition of 0.5 mol % of Ni(acac)$_2$ and 0.5 mol % of dppp (dppp=1,3-bis(diphenylphosphino)propane) and 1 mol % of triphenylphosphine, the reaction solution was heated to 100° C. and subsequently stirred at this temperature for 10 minutes. 8 l/h of acetylene were then introduced into the reaction solution at 100° C. and atmospheric pressure for 1.5 hours. Work-up by distillation gave dimethyl vinylphosphonate in a yield of 80%.

Example 2 (Comparative Example)

27.50 g of dimethyl phosphite were admixed with 27 ml of tetraethylene glycol dimethyl ether in a three-necked flask provided with an internal thermometer, condenser and gas inlet tube and the mixture was degassed under argon. After addition of 0.5 mol % of Ni(acac)$_2$ and 1 mol % of dppp, the reaction solution was heated to 100° C. and then stirred for 10 minutes at this temperature. 8 l/h of acetylene were then introduced into the reaction solution at 100° C. and atmospheric pressure for 1.5 hours. Work-up by distillation gave dimethyl vinylphosphonate in a yield of 80%.

What is claimed is:

1. A process for preparing an alkenylphosphonic acid derivative by reacting a phosphonic acid derivative with an alkyne in the presence of a catalyst complex system, wherein the catalyst complex system comprises
    (a) nickel,
    (b) a phosphine having at least two trivalent phosphorus atoms and in addition
    (c) a phosphine having one trivalent phosphorus atom
wherein the phosphine having at least two trivalent phosphorus atoms (b) is a phosphine of the formula (I)

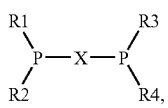

(I)

where $R^1$, $R^2$, $R^3$ and $R^4$ are each, independently of one another, a carbon-containing organic radical and X is a carbon-containing organic bridging group,
wherein the phosphonic acid derivative is represented by the formula (II)

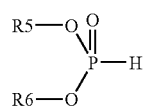

(II)

where $R^5$ and $R^6$ are each, independently of one another, a carbon-containing organic radical,
wherein the alkyne is represented by the formula (III)

(III)

where $R^7$ and $R^8$ are each, independently of on another, hydrogen or a carbon-containing organic radical and where $R^7$ and $R^8$ may optionally be joined to one another, and
wherein the phosphine having one trivalent phosphorus atom (c) is a phosphine of the formula (IV)

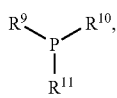

(IV)

where $R^9$, $R^{10}$ and $R^{11}$ are each, independently of one another, a carbon-containing organic radical.

2. A process as claimed in claim 1, wherein the molar ratio of nickel:(phosphine having at least two trivalent phosphorus atoms):(phosphine having one trivalent phosphorus atom) is 1:(0.5-2):(1-4).

3. A process as claimed in claim 1, wherein, in the phosphine (I), $R^1$, $R^2$, $R^3$ and/or $R^4$ are each, independently of one another, an unsubstituted or substituted $C_3$-$C_{12}$ alkyl radical in which not more than one atom from the group consisting of hydrogen, fluorine, chlorine, bromine and iodine is bound to the α-carbon atom;
    and/or $R^1$, $R^2$, $R^3$ and/or $R^4$ are each, independently of one another, an unsubstituted or substituted aromatic radical which has 6 ring atoms and in which one, two or three ring atoms may be replaced by nitrogen; and/or $R^1$ together with $R^2$ and/or $R^3$ together with $R^4$ forms an unsubstituted or substituted, aliphatic, aromatic or araliphatic group having from 4 to 7 carbon atoms in the chain and a total of not more than 30 carbon atoms.

4. A process as claimed in claim 1, wherein X in the phosphine (I) is an unsubstituted or substituted, aliphatic, aromatic or araliphatic group which has from 1 to 8 atoms in the chain and a total of not more than 20 carbon atoms.

5. A process as claimed in claim 1, wherein $R^1$ to $R^4$ in the phosphine (I) are each a 2-methyl-2-propyl group or are each a phenyl group and X is a 1,2-ethylene, 1,3-propylene, 1,4-butylene or o-xylylene group.

6. A process as claimed in claim 1, wherein, in the phosphine (IV), $R^9$, $R^{10}$ and/or $R^{11}$ are each, independently of one another, an unsubstituted or substituted $C_3$-$C_{12}$ alkyl radical in which not more than one atom from the group consisting of hydrogen, fluorine, chlorine, bromine and iodine is bound to the α-carbon atom;
    and/or $R^9$, $R^{10}$ and/or $R^{11}$ are each, independently of one another, an unsubstituted or substituted aromatic radical which has 6 ring atoms and in which one, two or three ring atoms may be replaced by nitrogen;
    and/or $R^9$ together with $R^{10}$ forms an unsubstituted or substituted, aliphatic, aromatic or araliphatic group having from 4 to 7 carbon atoms in the chain and a total of not more than 30 carbon atoms.

7. A process as claimed in claim 1, wherein the catalyst complex system is prepared by combining an Ni(0) complex and the two phosphines (b, c) or by combining an Ni(II) compound, a reducing agent and the two phosphines (b, c).

8. A process as claimed in claim 1, wherein from 0.01 to 10 mol % of nickel of the catalyst complex system based on the phosphonic acid derivative to be reacted is used.

9. A process as claimed in claim 1, wherein the reaction is carried out at from 20 to 150° C. and a pressure of from 0.05 to 2.5 MPa abs.

10. A process as claimed in claim 1, wherein the phosphonic acid derivative used is the dimethyl ester, the diethyl ester, the dipropyl ester, the dibutyl ester, the di(2-ethylhexyl) ester or the diphenyl ester of phosphonic acid.

11. A process as claimed in claim 1, wherein the alkyne used is ethyne or propyne.

12. A process as claimed in claim 1 for preparing a dialkyl vinylphosphonate by reacting a corresponding dialkyl phosphonate with acetylene.

* * * * *

UNITED STATES PATENT AND TRADEMARK OFFICE
CERTIFICATE OF CORRECTION

| | | |
|---|---|---|
| PATENT NO. | : 7,399,876 B2 | Page 1 of 1 |
| APPLICATION NO. | : 10/977436 | |
| DATED | : July 15, 2008 | |
| INVENTOR(S) | : Kessinger et al. | |

It is certified that error appears in the above-identified patent and that said Letters Patent is hereby corrected as shown below:

In claim 6, column 12, line 32, "$C_3\_C_{12}$" should read --$C_3$—$C_{12}$.--

Signed and Sealed this

Seventh Day of October, 2008

JON W. DUDAS
*Director of the United States Patent and Trademark Office*